United States Patent [19]

Slaton

[11] 4,228,678
[45] Oct. 21, 1980

[54] SURFACTANT CONCENTRATION DETECTOR

[75] Inventor: Clifton F. Slaton, Louisville, Ky.

[73] Assignee: Colgate-Palmolive Company, New York, N.Y.

[21] Appl. No.: 64,690

[22] Filed: Aug. 8, 1979

[51] Int. Cl.$^3$ ............................................. G01N 13/02
[52] U.S. Cl. ..................................... 73/64.4; 250/573
[58] Field of Search ..................... 73/64.4; 250/573; 356/426, 436, 440

[56] References Cited

U.S. PATENT DOCUMENTS

| 2,710,539 | 6/1955 | Pollack | 73/64.4 |
| 3,483,737 | 12/1969 | Jennings, Jr. et al. | 73/64.4 |
| 4,135,100 | 1/1979 | Harada et al. | 250/573 |

Primary Examiner—Gerald Goldberg
Assistant Examiner—Joseph W. Roskos
Attorney, Agent, or Firm—Herbert S. Sylvester; Murray M. Grill; John A. Stemwedel

[57] ABSTRACT

An apparatus for detecting the concentration of a surfactant in a liquid solution comprising a wheel rotatably mounted in a tank and having a portion which extends outwardly thereof. A series of progressively larger holes arranged on a circle concentric with the axis of rotation of the wheel are formed therein as are notches in the periphery of the wheel. Photoelectric cells are used to count the films formed across the holes and the notches in the wheel to provide an indication of the concentration of a surfactant.

6 Claims, 2 Drawing Figures

U.S. Patent  Oct. 21, 1980  4,228,678
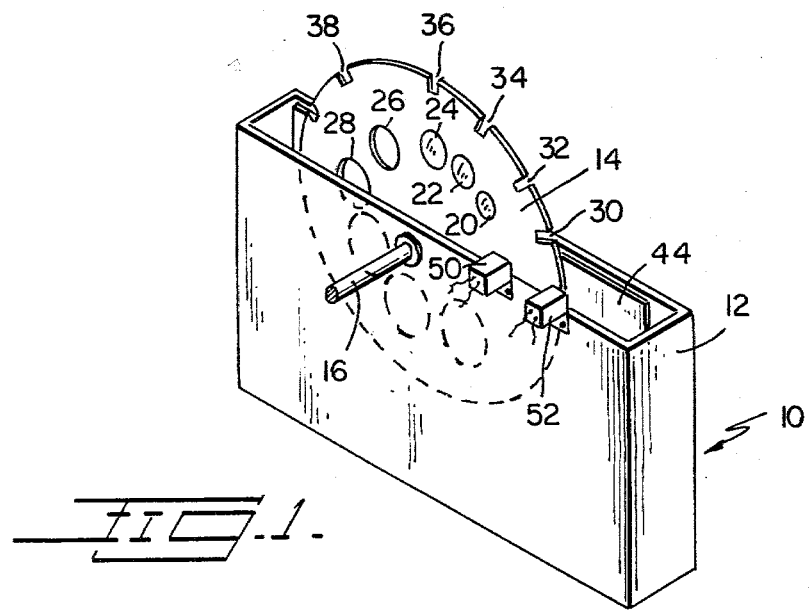
_FIG._1_.
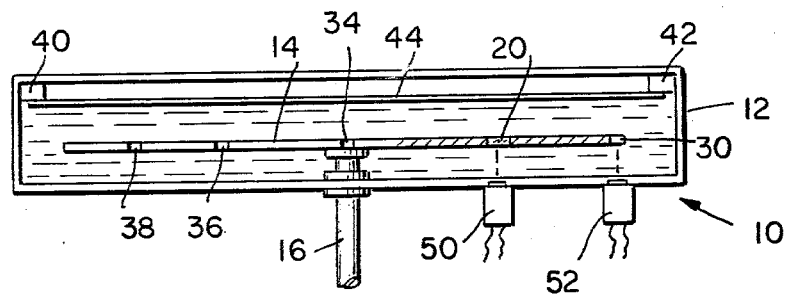
_FIG._2_.

SURFACTANT CONCENTRATION DETECTOR

BACKGROUND OF THE INVENTION

1. Field of the Invention

This invention relates to an apparatus for detecting the concentration of a solution by visual means.

2. Description of the Prior Art

In the past various apparatus for detecting the concentration of solutions by surface tension methods have been utilized. In U.S. Pat. No. 3,483,737 to Jennings, Jr. et al, entitled "Apparatus for Measuring Interfacial Tension," there is disclosed a rotary wheel having openings therein across which films can form. In U.S. Pat. No. 2,473,553 to Stokes, entitled "Method of and Apparatus for Measuring the Film Strength of Liquids," there is disclosed photoelectric means for measuring the concentration of a liquid.

SUMMARY OF THE INVENTION

The present invention overcomes the disadvantages of the prior art by providing visual means for detecting films across a series of different sized holes while also detecting the passing of slots in the periphery of the wheel corresponding to the holes so that the number of films counted per full rotation of the wheel may be easily obtained based on a continued series of optical counting and continuous rotation of the wheel.

The present invention involves a wheel rotatably mounted in a tank and having a portion thereof extending thereabove. Progressively larger holes arranged on a circle concentric with the axis of rotation of the wheel are formed therein as well as notches in the periphery of the wheel. A baffle is arranged in the tank to prevent foaming. Photoelectric cells are used to count the passing of the notches as well as the number of films formed across the holes due to surface tension. The output of the photoelectriccells will then provide a computation of the surface tension or a signal or alarm as to a change in the composition of the liquid being monitored.

BRIEF DESCRIPTION OF THE DRAWING

FIG. 1 is a perspective view of an embodiment of the invention; and,

FIG. 2 is a horizontal sectional view illustrating the relative arrangement of parts.

DETAILED DESCRIPTION OF THE INVENTION

With continuing reference to the accompanying drawing, wherein like reference numerals designate similar parts throughout the various views, reference numeral 10 generally designates the apparatus constructed in accordance with the present invention which includes a tank 12 open at the top and having a wheel 14 mounted on a shaft 16 journalled in the tank and adapted to be rotated by any suitable slow moving power source. The wheel 14 has a series of progressively larger holes 20, 22, 24, 26, 28, etc. formed therein on a circle which is concentric with the axis of rotation of the wheel 14. In alignment with the holes 20, 22, etc. and corresponding thereto and opening into the periphery of the wheel are a plurality of notches 30, 32, 34, 36, 38, etc. An inlet 40 and an outlet 42 for the solution to be tested is provided and between the inlet 40 and the outlet 42 and the wheel 14 is a baffle 44 which serves to prevent foaming at the wheel 14 which might reduce surface tension. Photoelectric cells 50 and 52 are mounted on the tank opposite a source of illumination, not shown. The photoelectric cell 50 is disposed to monitor and record the films across the holes 20, 22, etc. as the wheel is slowly rotated. The photoelectric cell 52 is designed to monitor the passing of each of the notches 30, 32, etc. The output of the photoelectric cells are connected to a logic circuit not shown, which counts the number of films formed per rotation of the wheel to give an analog output which ultimately corresponds to the surfactant concentration of the surfactant liquid solution being monitored. Of course, the circuit may be arranged to provide an alarm at a change of the concentration of the surfactant.

What is claimed is:

1. An apparatus for detecting the concentration of a surfactant liquid solution comprising a tank, means for delivering the liquid solution to said tank, a wheel rotatable in said tank, said wheel having a series of progressively larger holes therethrough, said holes being centered on a circle concentric with the axis of rotation of said wheel, said wheel having notches in the periphery thereof corresponding to each of said holes, a portion of said wheel rising out of said tank, first photocell means directed at said wheel for detecting films formed across any of said holes, second photocell means for counting said notches to time said wheel, and means for slowly rotating said wheel.

2. An apparatus according to claim 1, including baffle means between said means for delivering said liquid solution and said wheel for reducing foaming.

3. An apparatus for detecting the concentration of a liquid solution comprising a tank, a wheel rotatably mounted in said tank so that portions thereof rise out of said tank, a series of progressively larger holes in said wheel, notches in said wheel corresponding to said holes, first photocell means for counting the holes having films thereacross when said wheel rises above said tank, and second photocell means for counting said notches to time the speed of said wheel.

4. An apparatus according to claim 3, wherein said notches are formed in the periphery of said wheel.

5. An apparatus according to claim 4, including baffle means for reducing foaming of said liquid solution in said tank.

6. An apparatus according to claim 3, wherein said notches are formed in the periphery of said wheel, and baffle means for reducing foaming of said liquid solution in said tank.

* * * * *